United States Patent
Reimann et al.

[19]

[11] Patent Number: 5,899,401
[45] Date of Patent: May 4, 1999

[54] COUNTERBALANCE DEVICE, IN PARTICULAR FOR A MEDICAL X-RAY UNIT, HAVING PLURAL SAFETY DEVICES

[75] Inventors: Rolf Reimann; Thomas Schmitt, both of Forchheim, Germany

[73] Assignee: Siemens Aktiengesellschaft, Munich, Germany

[21] Appl. No.: 08/921,246

[22] Filed: Aug. 29, 1997

[30] Foreign Application Priority Data

Aug. 30, 1996 [DE] Germany ................. 196 35 236

[51] Int. Cl.⁶ ........................................ B65H 75/48
[52] U.S. Cl. ................................ 242/372; 242/382.1
[58] Field of Search ............................ 242/372, 375, 242/375.2, 378, 382.1, 382.4; 188/82.7, 69, 82.6

[56] References Cited

U.S. PATENT DOCUMENTS

| | | | |
|---|---|---|---|
| 1,933,925 | 11/1933 | Norling | 242/375.1 |
| 1,941,880 | 1/1934 | Earll | 242/382 |
| 2,078,489 | 4/1937 | Forss | 242/382.4 |
| 2,094,182 | 9/1937 | Nash | 242/375.1 |
| 2,801,814 | 8/1957 | Fischer et al. | 242/372 |
| 3,052,426 | 9/1962 | Avis | 242/372 |
| 3,384,321 | 5/1968 | Becker et al. | 242/372 |
| 3,625,450 | 12/1971 | Lloyd, Jr. | 242/86 |
| 4,123,013 | 10/1978 | Bottrill et al. | 242/107 |
| 4,303,208 | 12/1981 | Tanaka | 242/107 |
| 4,346,858 | 8/1982 | Hollowell et al. | 242/107 |
| 4,489,223 | 12/1984 | Puckett et al. | 191/12.2 R |
| 4,597,546 | 7/1986 | Yamamoto et al. | 242/107.4 A |
| 4,813,304 | 3/1989 | Kobayashi | 74/501.5 R |
| 5,452,862 | 9/1995 | Ray | 242/372 |

FOREIGN PATENT DOCUMENTS

| | | | |
|---|---|---|---|
| 712240 | 6/1965 | Canada | 242/372 |
| 4420192 | 12/1995 | Germany . | |
| 936180 | 9/1963 | United Kingdom | 242/372 |

*Primary Examiner*—Donald P. Walsh
*Assistant Examiner*—Minh-Chau Pham
*Attorney, Agent, or Firm*—Sughrue, Mion, Zinn, Macpeak & Seas, PLLC

[57] ABSTRACT

Counterbalance device (1), in particular for a medical X-ray device, with a drum (2) which is at least partly encapsulated in a housing (12) and is mounted so that it can rotate in the housing on a stationary shaft (11). The drum has an integrated first spring element (7) which applies a bias to the drum, and a first cable (5) which supports a weight (40). The cable is guided in a groove (3) on the drum and can be wound or unwound around the drum. An independent second spring element (8) is connected within the drum in parallel to the first spring element. A second cable is guided in an additional groove (4) on the drum and is connected to the weight. As a result, there is a separate safety device for each spring element and each cable, to prevent the uncontrolled descent of the weight in the event that the spring element and/or the coil breaks or fails.

23 Claims, 2 Drawing Sheets

COUNTERBALANCE DEVICE, IN PARTICULAR FOR A MEDICAL X-RAY UNIT, HAVING PLURAL SAFETY DEVICES

FIELD OF AND BACKGROUND OF THE INVENTION

The invention relates to new and useful improvements in a counterbalance device. More particularly, the invention relates to a counterbalance device for a medical X-ray unit, with a drum which is at least partly encapsulated in a housing. The drum is mounted so that it can rotate in the housing on a stationary shaft and is provided with an integrated first spring element which applies a bias to the drum. The drum is further provided with a cable which supports a weight, which is guided in a groove on the drum, and which can be wound around or unwound from the drum.

Similar counterbalance devices are used in the medical equipment industry, for example, to counterbalance the dead weight of an X-ray emitter located on a telescoping column guided in the ceiling, so that the height of the X-ray unit can be easily and simply adjusted manually or by mechanical means. Such a device is described in DE 43 11 802 A1 and in DE 44 20 192 A1, for example. As a result of the bias applied by a spring element, a force which opposes the weight of the X-ray emitter is applied to a cable, and results in a counterbalancing of the weight of the unit. It thereby becomes possible to move the weight easily by applying only a small amount of force. Such a counterbalance unit must comply with a number of requirements, particularly in terms of safety. The unit should guarantee that, in the event of any failure or malfunction of the device, the weight does not descend in an uncontrolled and undecelerated manner, which could not only damage the portion of the device being supported or the unit which contains this device, but naturally could also injure a patient who might be lying underneath the weight. Such a failure or malfunction could occur due to the spring element as well as the cable. The prior art, however, does not describe a counterbalance device which fully and satisfactorily meets all safety requirements.

OBJECTS OF THE INVENTION

It is therefore one object of the invention to provide a counterbalance device that provides an enhanced degree of safety in the event of a failure or malfunction in the counterbalance device. It is a further object of the invention to provide a counterbalance device that ensures a controlled and reliable response as a result of a failure or malfunction.

SUMMARY OF THE INVENTION

These and other objects of the invention are achieved by the teaching of claim 1. Particularly advantageous refinements of the invention are the subject matter of the dependent claims.

The counterbalance device claimed by the invention is characterized by the provision of plural spring elements and cables. The provision of a second spring element working simultaneously with the first spring element is advantageous in that, in the event of any breakage or failure of the first spring element, the second spring element is fully effective, and at least partly counterbalances the suspended load, so that the load can descend at only about 0.5 g. If there were only one spring element, on the other hand, the weight would drop in an undecelerated manner. As a result of providing an individual safety device for each spring and cable, the distance by which the weight can descend is advantageously limited, namely until the safety device engages. In other words, the device claimed by the invention guarantees that, in the event of a failure of the spring element, the weight falls slowly and for only a very short distance, which means that any damage to the equipment or any injury to the patient lying underneath etc. can be advantageously prevented.

Similar advantages can be achieved by means of the second cable provided by the invention. This second cable is capable of catching the falling load, which could perhaps otherwise fall, in the event of a breaking of the first cable. Because this second cable, fashioned, e.g., as an arresting cable, is, as a rule, somewhat longer than the first load-bearing cable, it can be formed, e.g., into a loop, and can be extended in the event of a rupture or malfunction of the first cable, whereby the length of the second cable limits the maximum descent. The safety device that is actuated in the event of a failure of the first cable guarantees that the cable drops by no more than the difference between the cable lengths, and is then supported by the second cable. Also, when the safety device engages sufficiently rapidly, the safety device advantageously prevents a descent which is any further than the difference in length between the two cables. The counterbalance device claimed by the invention therefore represents a comprehensive safety system which provides sufficient protection against a dangerous or uncontrolled descent of the weight.

The invention teaches that the safety devices can be formed as locking devices which are located on the drum, and can have spring-loaded movable locking means which can be moved between a retracted, non-operating position and an operating position in which they project out from the outer cylindrical surface of the drum, e.g. through windows in the drum. These locking devices interact with preferably rib-shaped locking projections which are provided on the generally cylindrically-shaped inside wall of the housing, just beyond the outer surface of the drum. The locking projections are held in the non-working position by the respective intact spring elements or cables, and are released into their working position in the event of a failure of the spring element or cable. A particular advantage of the use of the spring-loaded locking devices claimed by the invention is the rapid engagement of the safety device. This rapid engagement is guaranteed by the fact that the respective safety device is coupled directly to the respective spring element or cable, so that a failure of the spring or cable results in the actuation of the safety device directly and without the interposition of any additional elements.

Primarily if, on an X-ray machine for example, the X-ray emitter has fallen to a short distance above the patient, the patient must be protected from the effects of any possible failure or malfunction. Thus, when the safety device engages, it should preferably be possible to hoist the weight back up, e.g. so that the patient can climb off the table. To guarantee this capability, the invention teaches that the locking means and locking projections are fashioned so that when they interact, the drum is able rotate in only one direction with respect to the housing. An engagement therefore results in a locking in only one direction, namely in the direction in which the weight would otherwise fall. In the other direction, however, the drum can be moved inside the housing so that the weight can be raised. On account of the presence of a plurality of locking projections, a continuous engagement, and thus continuous protection, is guaranteed even as the weight is raised. Because the cable which supports the weight is always retracted by the action of at least one spring element, regardless of the type of failure, the weight thereby advantageously remains in the raised position.

The invention teaches that the locking means associated with one of the spring elements can be realized in the form of a locking pawl which, in the non-working position, is folded into the drum by an engagement device located on the spring element. When a prestress is applied to the spring element, this engagement device engages a mating piece which is provided on the locking pawl. The invention further teaches that the locking means associated with the cable can be realized in the form of another type of locking pawl. This locking pawl can be fashioned as a spring-loaded pin or similar element which projects into the groove guiding the cable. The spring-loaded pin or similar element is pushed into the base of the groove by the intact cable, thereby retracting the locking pawl. In addition to the safety advantages of the locking means, it is also particularly advantageous if this locking means performs an indicator function. If, in the event of a failure of the spring or cable, the locking means is actuated during an upward movement of the weight, which in that case is the only allowable movement, an audible sound like that produced by a ratchet is generated as the locking means runs over the various locking projections, thereby indicating the occurrence of a break or failure. A failure is also indicated by the fact that the weight can no longer be pulled downward.

An additional problem of such counterbalance devices is the generation of noise when the counterbalance devices are actuated. This noise is caused on one hand by the running of the cables in the grooves, and on the other hand by the action of the springs. To counteract the noise, stemming from the action of the cable, the invention teaches that the grooves can be oriented at an angle to the axis of rotation toward a reference point, preferably the point of contact of the respective cable on a downstream pulley. In this embodiment, the cable can thus exit the groove without generating excessive friction against the walls of the groove. According to this design, the groove walls are oriented so that they are directed toward the vanishing point, formed e.g. by a downstream pulley, thereby resulting in a significant noise reduction.

To reduce noise resulting from activation of the spring elements, the invention teaches that friction-reducing washers made of plastic are located above and/or below the spring elements and/or between the spring elements. These friction-reducing washers prevent the individual turns of the strip-shaped spring elements from tipping and rubbing against one another or snagging on each other, or rubbing against the drum. The invention also teaches that a plastic strip may be located between the turns of each spring element, thereby damping the friction of the individual turns against one another. Alternatively or in addition to the measures described above, the invention further teaches that each spring element can have a friction-reducing coating, in particular a lubricant coating or Teflon.

To be able to realize a correct counterbalance that corresponds to the actual conditions of the specific application, the invention further teaches that the path (characteristic) of at least the groove which guides the first cable can be selected as a function of the characteristic of the spring elements and of the weight, so that a very precise counterbalancing can be achieved by means of such a guide groove, on account of the lever action it represents, in connection with the torque exerted by the spring elements.

To make possible the use of the exact same counterbalance device to equalize different loads within certain limits, the invention further teaches that the grooves define paths which are at different distances from the axis of rotation. Because the distance from the groove base to the axis of rotation is the origin of the lever action which ultimately contributes to the counterbalancing action, it is possible to counterbalance different weights by selecting a groove path which has the appropriate differences in elevation. The first cable, which supports the weight, is advantageously laid simply into the corresponding groove designed to counterbalance a specified weight. The second cable then runs in the other, e.g., adjacent, respective groove. The safety function is not thereby adversely affected, because the position of the groove is not important for the safety function.

The invention further makes it possible for a service technician to fix the weight in a specified position, regardless of any failures of the cables or springs which may have occurred, without having the weight move any further. According to the invention, fastening means, which are engaged by pins or similar elements, can be fastened on the housing and can be effectively connected to the drum. These can be embodied in particular as a stud or similar element which, according to the invention, can be actuated manually and/or automatically, most preferably electro-magnetically.

To guarantee manual operation, means, such as threaded borings in the housing, may be provided for directly connecting a motor-driven hoisting device to the counterbalance device. The direct connection makes it possible to eliminate the external pulley, which was necessary in similar devices of the prior art, and by means of which the cable was guided and with which the hoisting device was engaged. The invention, on the other hand, teaches that a direct engagement on the drum is possible, an additional advantage of which is that no cable slip occurs. Cable slip has been a common disadvantage of similar prior art devices.

The invention teaches provision of an automatic braking device, comprising an electromagnetically releasable permanent magnet which is installed so that when it is not energized, it engages the drum and exerts a braking action on it. When the electromagnet is energized, on the other hand, it detaches from the drum under its own weight. This arrangement is most appropriate when, to detach the magnet from the weight, on the one hand, only a small current needs to be applied to affect the demagnetization, so that the magnet advantageously automatically falls away from the drum, and no additional measures are necessary to achieve this release. On the other hand, there is a guarantee that, in the event of any power failure, the magnet advantageously engages the drum immediately.

The invention further teaches that the drum itself can be made of plastic or a metal alloy, preferably a magnesium alloy. Furthermore, the drum can be mounted on the shaft in a cantilevered fashion, i.e., at only one point, which is advantageous compared to the two-point mounting used in similar devices in the prior art, most particularly with regard to the extremely precise tolerances etc. which are required.

BRIEF DESCRIPTION OF THE DRAWINGS

The invention and further advantageous refinements of the invention according to the features of the dependent claims are explained in more detail below with the aid of exemplary embodiments in the drawings, in which:

FIG. 1 shows a counterbalance device, e.g., for a medical X-ray unit, having an essentially cylindrical drum 2, on the one truncated cone-shaped end of which two grooves 3, 4 have been milled. Two cables 5, 6 are guided in these grooves, one of which is the actual load-bearing cable for supporting a weight 40, and the other of which is the arresting cable, which engages in the event of any failure of the first cable. The grooves 3, 4 run on a spiral path, preferably oriented in the direction of a downstream pulley or the like. Inside the drum there are two spring elements 7, 8 which are made of strip spring steel. The spring elements are held together at the periphery of the drum by a clamp 9. The overall drum apparatus is rotationally mounted, preferably in cantilevered fashion, by means of two ball bearings 10 on a stationary shaft 11 that is fastened in a housing 12, indicated in FIG. 1 merely schematically by broken lines. In other words, when there is any tension on a cable, the drum 2 rotates around the shaft 11. The cylindrical drum recess is closed on top with a cover 13. Friction-reducing plastic washers 14 are provided between the spring elements 7, 8 and at the transitions to the drum 2 and to the cover 13, over which the edges of the individual turns of the spring move when the drum 2 is rotated.

FIG. 1 also shows a safety device 15 associated with the lower spring element 8. The individual safety device 15 associated with the upper spring element 7 is preferably located on the opposite side of the first safety device, as shown in FIG. 2. Each safety device 15 consists of a locking pawl 16 which is installed by means of a pin 17 so that it can pivot on the cylindrical portion of the drum 18, as shown most particularly in FIG. 3. The spring-loaded locking pawl 16 can pivot between a non-working position in which it is pivoted into the drum area 18, and a working position in which it projects out of the drum area 18, e.g. through a window. In the working position into which it moves e.g. as the result of its associated spring element breaking, the locking pawl 16 engages with locking projections 21 which are provided on the inner wall 20 of the housing 12 (shown in FIG. 2). The locking pawl 16 and the locking projections 21 thereby function together to block any rotation of the drum 2 in the direction indicated by the Arrow A in FIG. 2, corresponding to the direction of descent of the weight. On the other hand, a movement in the opposite direction (Arrow B in FIG. 2), which is executed when the weight is being raised, is still possible, because the presence of the locking projections 21 makes possible a ratchet-like movement past the locking pawl 16.

Figure 1:
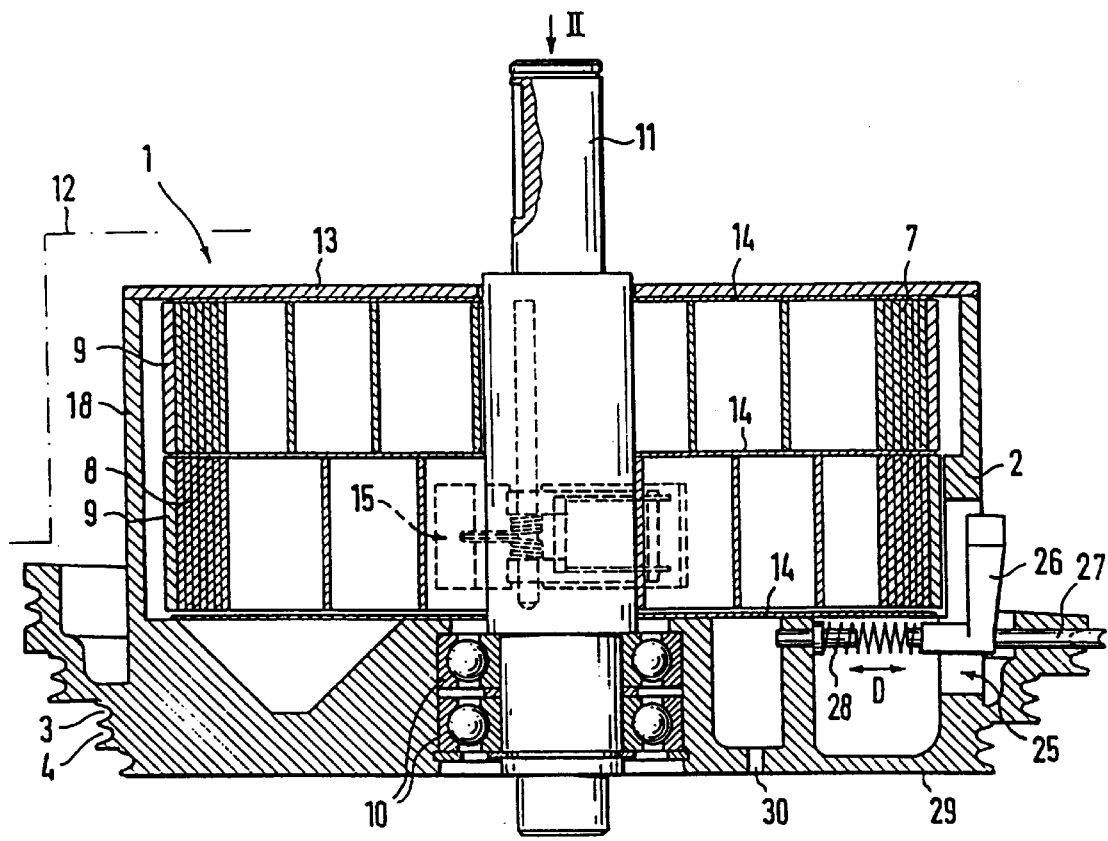
FIG. 1 shows a cross section through the counterbalance device according to one embodiment of the invention, showing only a portion of the housing.
Figure 3:
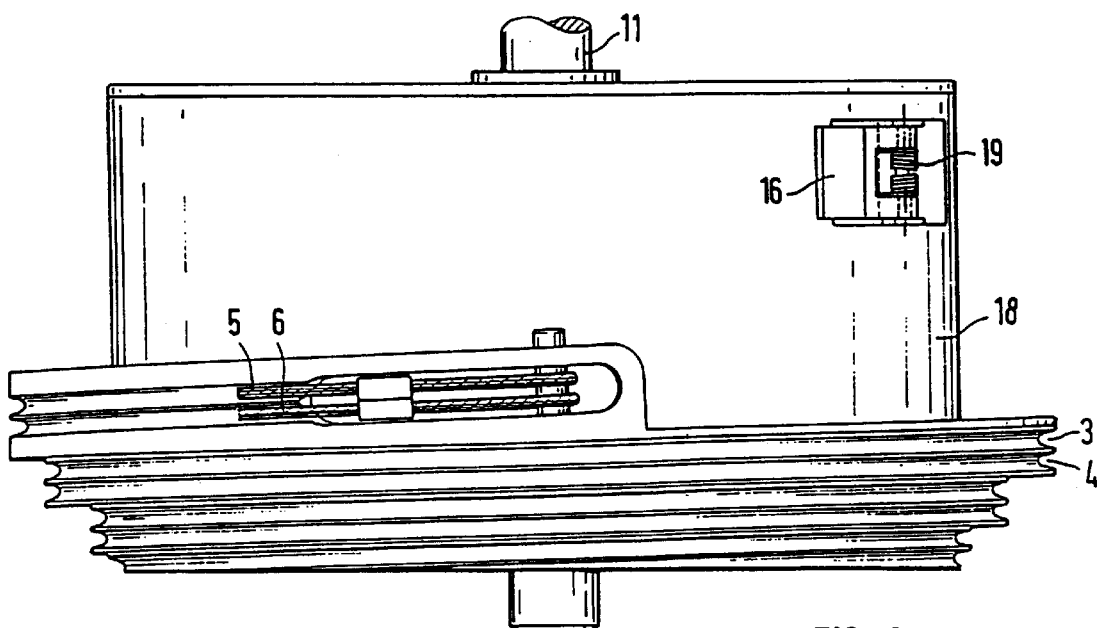
FIG. 3 is a side view of the counterbalance device of FIGS. 1 and 2, from the direction indicated by the Arrow III in FIG. 2.

To move the locking pawl 16 into the non-operating position, on each spring element in the vicinity of the bridge 9 there is an engagement device 22, the forward edge of which is beveled in a wedge shape. After the installation of the spring elements 7, 8 and after the fastening of one of their inner ends 23 to the shaft 11, the shaft is ultimately rotated by means of a worm gear (not shown) in the direction indicated by the Arrow B, to prestress the spring elements. This prestress is necessary so that a force can be transmitted to the weight by the spring elements, regardless of the current position of the weight. The rotation of the shaft 11 results in a movement of the engagement device 22 in the direction indicated by the Arrow C, so that it travels toward the locking pawl 16. A mating piece 24, which is also wedge-shaped, is realized on the locking pawl 16. When the engagement device 22 engages the mating piece 24, the locking pawl 16 is pulled inside the drum, i.e., into the non-working position.

Figure 2:
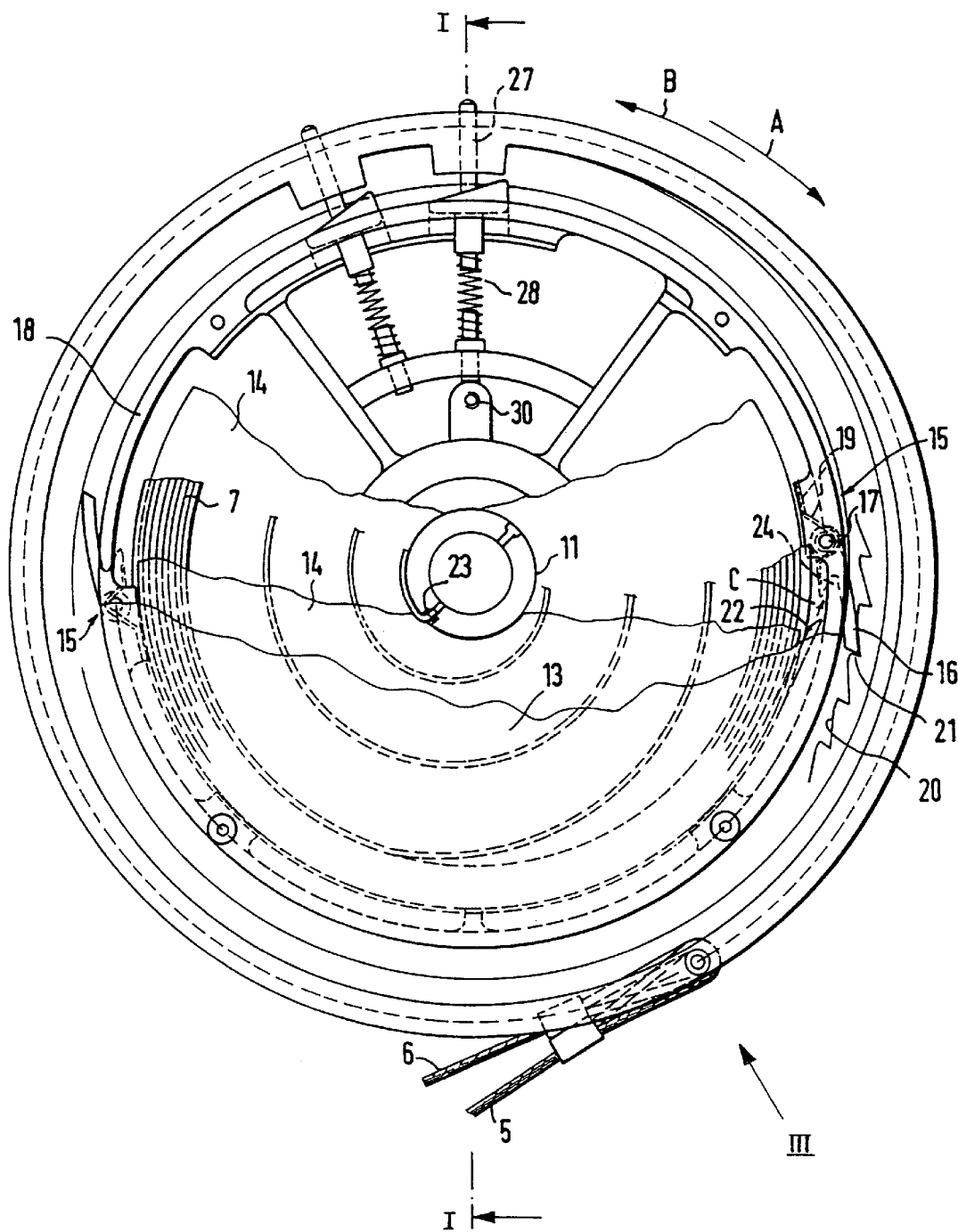
FIG. 2 shows an overhead view of the device illustrated in FIG. 1, from the direction of the Arrow II indicated in FIG. 1 and in partial cutaway.

When the locking pawl 16 is required to perform its safety function in the event of a failure or break of the spring element, the action of the spiral spring 19 causes the locking pawl 16 to be pushed back into the working position illustrated in FIG. 2. In the event of a break, the spring element relaxes in a fraction of a second, which causes the engagement device 22 to move in the direction opposite to the direction indicated by the Arrow C, thereby releasing the locking pawl 16. Because each spring element 7, 8 has its own safety device, the uncontrolled descent of the load is prevented in the event of any spring break failure.

FIG. 1 also shows a safety device 25 associated with a cable, whereby here again, there is a safety device for each cable, as shown in FIG. 2. This safety device consists of a locking pawl 26 which, in the extended position, is also engaged in the locking projections 21 and blocks any movement. The locking pawl 26 is connected to a pin 27 which is spring-loaded by a compression spring 28 and projects into the corresponding groove 3, 4 as shown in FIG. 1. An intact cable guided in the groove presses this pin into the base of the groove, as a result of which the locking pawl 26 is also retracted. If the cable breaks, the pin 27 is released so that, as illustrated by the double arrow D in FIG. 1, the pin is pushed into the groove, which also results in the locking pawl 26 extending radially outward and thus engaging with the locking projections 21, thereby locking the drum. Because of the design of this safety device, a movement in the direction indicated by the Arrow B remains possible even when the safety device is engaged in the locking projections 21, because it can run over the locking projections like a ratchet. In other words, even in the event of a break in the cable, it is possible to move the weight upward to protect the patient.

FIG. 2 also shows threaded borings 30 which are provided on the underside 29 of the drum. These threaded borings 30 are spaced apart from one another and are used to connect a motor-driven hoisting device directly to the drum 2. This allows the drum and thus the weight to be moved by motor power. In the installed position, the counterbalance device shown in FIGS. 1 and 2 is rotated by 180 degrees from the illustrated position, so that the cover 13 on which the permanent magnet (not shown) is engaged forms the bottom cap of the drum.

The above description of the preferred embodiments has been given as an example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. Counterbalance device comprising:

a stationary shaft;

a drum rotatably mounted on said shaft and provided with a first groove and a second groove;

a housing at least partly encapsulating said drum;

a first spring element integrated into said drum and applying a bias to said drum;

a first cable for supporting a weight, said cable being guided in the first groove of said drum for winding or unwinding said first cable;

a second spring element integrated into said drum and operating in parallel with said first spring element;

a second cable guided in the second groove of said drum and attached to the weight;

a first safety device associated with said first spring element and actuated in the event of a failure of said first spring element for preventing an uncontrolled descent of the weight;

a second safety device associated with said second spring element and actuated in the event of a failure of said second spring element for preventing the uncontrolled descent of the weight;

a third safety device associated with said first cable and actuated in the event of a failure of said first cable for preventing the uncontrolled descent of the weight; and a fourth safety device associated with said second cable and actuated in the event of a failure of said second cable for preventing the uncontrolled descent of the weight;

whereby each said safety device functions independent of remaining ones of said safety devices to prevent the uncontrolled descent of the weight.

2. Counterbalance device as claimed in claim 1, wherein:

said drum comprises an outer, generally cylindrical surface;

each of said safety devices comprises a locking device disposed on said drum, said locking device comprising a spring-loaded lock movable between a retracted, non-working position, in which said spring-loaded lock is retracted within said drum, and an extended, working position in which said spring-loaded lock projects from the outer cylindrical surface of said drum;

said housing comprises a generally cylindrical inner wall provided with a plurality of locking projections arranged around the inner wall of said housing; and said spring loaded lock, in the working position, engages at least one of said locking projections.

3. Counterbalance device as claimed in claim 2, wherein:

said spring-loaded lock of said first safety device is held in the non-working position by said associated first spring element when said first spring element is intact and is released into the working position in the event of the failure of said first spring element;

said spring-loaded lock of said second safety device is held in the non-working position by said associated second spring element when said second spring element is intact and is released into the working position in the event of the failure of said second spring element;

said spring-loaded lock of said third safety device is held in the non-working position by said associated first cable when said first cable is intact and is released into the working position in the event of the failure of said first cable;

said spring-loaded lock of said fourth safety device is held in the non-working position by said associated second cable when said second cable is intact and is released into the working position in the event of the failure of said second cable.

4. Counterbalance device as claimed in claim 2, wherein:

said locking projections are each rib-shaped; and said locking projections are disposed at regular intervals around the inner wall of said housing.

5. Counterbalance device as claimed in claim 2, wherein:

said spring-loaded lock of said first safety device, in the working position, engages said at least one locking projection such that said drum is rotatable around said shaft in only one rotational direction with respect to said housing.

6. Counterbalance device as claimed in claim 5, wherein:

said spring-loaded lock of said first safety device comprises a pawl, whereby said spring-loaded lock and said locking projections form a ratchet arrangement permitting said spring-loaded lock to move in only one tangential direction relative to said locking projections in the working position.

7. Counterbalance device as claimed in claim 6, wherein said pawl comprises a mating piece; and further comprising:

an engagement device connected to said first spring element and which, in the non-working position, retracts said pawl into said drum, whereby a prestress applied to said first spring element causes said engagement device to engage said mating piece of said pawl and thereby retract said pawl into said drum.

8. Counterbalance device as claimed in claim 2, wherein:

said spring-loaded lock of said third safety device comprises a pawl, whereby said spring-loaded lock and said locking projections form a ratchet arrangement permitting said spring-loaded lock to move in only one tangential direction relative to said locking projections in the working position.

9. Counterbalance device as claimed in claim 8., wherein:

said spring-loaded lock of said third safety device further comprises a projection coupled to said pawl;

in the working position, said projection projects into the first groove, which guides said first cable, causing said pawl to project from said drum and engage at least one of said locking projections; and in the non-working position, said projection is pushed into a base of the first groove by said first cable, causing said pawl to retract into said drum and disengage from said locking projections.

10. Counterbalance device as claimed in claim 2, wherein:

said spring-loaded lock of said third safety device comprises a spring-loaded pin that, in the working position, projects into the first groove, which guides said first cable, and, in the non-working position, is pushed into a base of the first groove by said first cable.

11. Counterbalance device as claimed in claim 1, wherein:

the first and second grooves extend at an angle to an axis of rotation of said drum and are oriented toward a reference point external to said drum and defined by a downstream location of at least one of said first cable and said second cable.

12. Counterbalance device as claimed in claim 1, wherein:

said drum comprises a plurality of first grooves and a plurality of second grooves;

the plurality of first grooves each defines a different respective distance from an axis of rotation of said drum;

the plurality of second grooves each defines a different respective distance from an axis of rotation of said drum; and said first cable and said second cable run selectively in one of the plurality of first grooves and one of the plurality of second grooves, respectively.

13. Counterbalance device as claimed in claim 12, wherein:

at least the plurality of first grooves are arranged such that, for a plurality of design weights supported by said first cable, respective lever actions defined by the first grooves essentially balance respective torques exerted by said first and second spring elements.

14. Counterbalance device as claimed in claim 1, further comprising:
friction-reducing plastic washers contacting said first spring element and said second spring element.

15. Counterbalance device as claimed in claim 1, further comprising:
plastic strips interposed between turns of said first spring element and turns of said second spring element, respectively.

16. Counterbalance device as claimed in claim 1, wherein:
said first spring element and said second spring element respectively comprise a friction-reducing coating.

17. Counterbalance device as claimed in claim 1, wherein:
said housing comprises at least one stud extendable towards said drum; and
said drum comprises an outer, generally cylindrical surface having at least one recess corresponding to said stud; and
the recess is located and shaped to receive said stud for fixing said drum to be stationary relative to said housing.

18. Counterbalance device as claimed in claim 17, wherein said stud is actuated through a manual, electrical or electromagnetic means to extend into the recess.

19. Counterbalance device as claimed in claim 1, wherein:
said drum comprises an outer, generally circular surface having at least one threaded boring located and shaped to receive a stud of a motor-driven hoisting device.

20. Counterbalance device as claimed in claim 1, further comprising:
an automatic braking device provided adjacent said drum and comprising an electromagnetically actuated permanent magnet which, in a non-energized state, engages with said drum, thereby braking the drum, and, in an energized state, detaches from said drum under its own weight.

21. Counterbalance device as claimed in claim 1, wherein:
said drum is constructed of a material selected from the group of: plastics and metal alloys.

22. Counterbalance device as claimed in claim 21, wherein:
said drum is constructed of a magnesium alloy.

23. Counterbalance device as claimed in claim 1, wherein:
said drum is mounted on said shaft only at one axial end of said drum.

* * * * *